US011315666B2

(12) United States Patent
Wang (10) Patent No.: US 11,315,666 B2
(45) Date of Patent: Apr. 26, 2022

(54) BLOCKCHAIN-BASED DATA PROCESSING METHOD AND DEVICE

(71) Applicant: Advanced New Technologies Co., Ltd., Grand Cayman (KY)

(72) Inventor: Shifeng Wang, Hanzhou (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 0 days.

(21) Appl. No.: 16/422,618

(22) Filed: May 24, 2019

(65) Prior Publication Data

US 2019/0279750 A1    Sep. 12, 2019

Related U.S. Application Data

(63) Continuation of application No. PCT/CN2018/087767, filed on May 22, 2018.

(30) Foreign Application Priority Data

May 24, 2017 (CN) .......................... 201710372331.1

(51) Int. Cl.
*G16H 10/60* (2018.01)
*G16H 15/00* (2018.01)
(Continued)

(52) U.S. Cl.
CPC ......... *G16H 10/60* (2018.01); *G06F 21/6245* (2013.01); *G16H 15/00* (2018.01);
(Continued)

(58) Field of Classification Search
USPC .................................................... 705/50–79
See application file for complete search history.

(56) References Cited

U.S. PATENT DOCUMENTS

| 6,519,624 B1 * | 2/2003 | Gruber ................ H04L 12/5692 709/200 |
| 2004/0133652 A1 * | 7/2004 | Miloushev .......... G06F 11/1076 709/214 |

(Continued)

FOREIGN PATENT DOCUMENTS

| CN | 101132463 | 2/2008 |
| CN | 102592074 | 7/2012 |

(Continued)

OTHER PUBLICATIONS

"How can I store data in ethereum blockchain?", (downloaded from https://ethereum.stackexchange.com/questions/7884/how-can-i-store-data-in-ethereum-blockchain and attached as PDF file, dated Apr. 2017 (Year: 2017).*

(Continued)

*Primary Examiner* — James D Nigh
*Assistant Examiner* — Margaret Neubig
(74) *Attorney, Agent, or Firm* — Fish & Richardson P.C.

(57) ABSTRACT

In an implementation, processing blockchain-based data is described. Data to be stored in a blockchain network is received at one or more processing devices of a blockchain node. A determination is made that an attribute of the data is of a particular type. In response to determining that the attribute of the data is of the particular type, a digest representing the data is generated. The digest is smaller in size than the data. The data is stored at a storage location in accordance with a mapping relationship between the digest and a first identifier of the data. An encrypted version of the digest is generated, by the one or more processing devices for storage on the blockchain network, using a private key of a public-private key pair corresponding to a second identifier of the data.

15 Claims, 6 Drawing Sheets

(51) Int. Cl.
- *G06F 21/62* (2013.01)
- *H04L 9/06* (2006.01)
- *H04L 9/08* (2006.01)
- *H04W 12/02* (2009.01)
- *H04L 29/06* (2006.01)
- *H04L 29/08* (2006.01)
- *H04L 67/12* (2022.01)

(52) U.S. Cl.
CPC .......... *H04L 9/0637* (2013.01); *H04L 9/0816* (2013.01); *H04L 63/0442* (2013.01); *H04L 63/123* (2013.01); *H04L 67/12* (2013.01); *H04W 12/02* (2013.01); *H04L 2209/38* (2013.01)

(56) References Cited

U.S. PATENT DOCUMENTS

| | | | |
|---|---|---|---|
| 2007/0282635 A1* | 12/2007 | Kereun | G16H 15/00 705/3 |
| 2014/0047513 A1* | 2/2014 | van 'T Noordende | H04L 63/0823 726/4 |
| 2015/0046192 A1* | 2/2015 | Raduchel | H04W 12/06 705/3 |
| 2016/0117471 A1 | 4/2016 | Belt et al. | |
| 2016/0321654 A1 | 11/2016 | Lesavich et al. | |
| 2016/0379330 A1 | 12/2016 | Powers et al. | |
| 2017/0048209 A1 | 2/2017 | Lohe et al. | |
| 2017/0076109 A1 | 3/2017 | Kaditz et al. | |
| 2017/0091397 A1 | 3/2017 | Shah | |
| 2017/0324711 A1* | 11/2017 | Feeney | H04L 9/3247 |
| 2018/0121620 A1* | 5/2018 | Bastide | G06F 16/334 |
| 2018/0227118 A1* | 8/2018 | Bibera | G06F 16/21 |

FOREIGN PATENT DOCUMENTS

| | | |
|---|---|---|
| CN | 106209877 | 12/2016 |
| CN | 106330431 | 1/2017 |
| CN | 106354994 | 1/2017 |
| CN | 106529177 | 3/2017 |
| CN | 106682530 | 5/2017 |
| CN | 106686008 | 5/2017 |
| CN | 107426170 | 12/2019 |
| IN | 201947018765 | 11/2019 |
| JP | 2007060336 | 3/2007 |
| WO | WO 2016065172 | 4/2016 |
| WO | WO 2017074017 | 5/2017 |
| WO | WO-2018100227 A1 * | 6/2018 ............ G06F 16/00 |

OTHER PUBLICATIONS

Huang, "Blockchain technology-based security of electronic health records," Chinese Journal of Library and Information Science for Traditional Chinese Medicine, Oct. 2016, 25(10):38-40, 46 (with English abstract).

PCT International Search Report and Written Opinion in International Application No. PCT/CN2018/087767, dated Aug. 7, 2018, 10 pages (with partial English translation).

Crosby et al., "BlockChain Technology: Beyond Bitcoin," Sutardja Center for Entrepreneurship & Technology Technical Report, Oct. 16, 2015, 35 pages.

Nakamoto, "Bitcoin: A Peer-to-Peer Electronic Cash System," www.bitcoin.org, 2005, 9 pages.

Extended European Search Report in European Application No. 18805030.6, dated Nov. 27, 2019, 8 pages.

PCT International Preliminary Report on Patentability in International Application No. PCT/CN2018/087767, dated Nov. 26, 2019, 10 pages (with English translation).

Xia et al., "BBDS: Blockchain-Based Data Sharing for Electronic Medical Records in Cloud Environments." Information, Apr. 2017, 8(2):1-16.

Qi et al., "BBDS: Blockchain-Based Data Sharing for Electronic Medical Records in Cloud Environments," MDPI Information, Mar. 2017, 16 pages.

* cited by examiner

BLOCKCHAIN-BASED DATA PROCESSING METHOD AND DEVICE

CROSS-REFERENCE TO RELATED APPLICATIONS

This application is a continuation of PCT Application No. PCT/CN2018/087767, filed on May 22, 2018, which claims priority to Chinese Patent Application No. 201710372331.1, filed on May 24, 2017, and each application is hereby incorporated by reference in its entirety.

TECHNICAL FIELD

The present disclosure relates to the fields of Internet information processing, medical and health, blockchain technologies, and in particular, to a blockchain-based data processing method and device.

BACKGROUND

With development of the medical technology and the big data technology, medical data of patients plays an increasingly important role in human health development. Therefore, how to manage the medical data of the patients and properly use the medical data of the patients becomes a key problem that needs to be solved.

In actual life, different medical institutions have their own medical data management systems. The medical data of the patients is managed by using the medical data management systems. It has been found through study that in practice, if a patient is treated in different medical institutions, medical data is generated in different medical institutions. Usually, the medical data is not shared between different medical institutions. To be specific, assume that patient A has visited a doctor in medical institution A (medical data is generated), and then the patient visits a doctor in medical institution B, the doctor in medical institution B cannot view the medical data generated for the patient in medical institution A, and can obtain the medical data only through strict examination and approval procedures, which is actually detrimental to the patient.

Therefore, how to share medical data between different medical institutions becomes an important problem.

SUMMARY

In view of this, implementations of the present disclosure provide a blockchain-based data processing method and device, to solve a problem of how to share medical data.

The following technical solutions are adopted in the implementations of the present disclosure.

An implementation of the present disclosure provides a blockchain-based data processing method, including: receiving, by a blockchain node, service data to be stored, and determining a data attribute of the service data; and if the data attribute of the service data is a text type, encrypting, by the blockchain node, the service data by using a private key in a predetermined public-private key pair corresponding to a user identifier included in the service data; or if the data attribute of the service data is an image type, determining, by the blockchain node, a digest of the service data, and encrypting the digest by using a private key in a predetermined public-private key pair corresponding to a user identifier included in the service data.

An implementation of the present disclosure provides a blockchain-based data processing method, including: receiving, by a blockchain node, service data to be stored, and determining a data attribute of the service data; and processing, by the blockchain node, the service data based on a configured processing rule corresponding to the data attribute, and sending a processing result to another blockchain node in a blockchain network.

An implementation of the present disclosure further provides a blockchain-based data processing device, including: a receiving unit, configured to receive service data to be stored, and determine a data attribute of the service data; and a processing unit, configured to: if the data attribute of the service data is a text type, encrypt the service data by using a private key in a predetermined public-private key pair corresponding to a user identifier included in the service data; or if the data attribute of the service data is an image type, determine a digest of the service data, and encrypt the digest by using a private key in a predetermined public-private key pair corresponding to a user identifier included in the service data.

An implementation of the present disclosure further provides a blockchain-based data processing device, including: a receiving unit, configured to receive service data to be stored, and determine a data attribute of the service data; and a processing unit, configured to process the service data based on a configured processing rule corresponding to the data attribute, and send a processing result to another blockchain node in a blockchain network.

At least one of the previous technical solutions used in the implementations of the present disclosure can achieve the following beneficial effects:

In the implementations of the present disclosure, when receiving the service data to be stored, the blockchain node determines the data attribute of the service data; and if the data attribute of the service data is a text type, the blockchain node encrypts the service data by using the private key in the predetermined public-private key pair corresponding to the user identifier included in the service data; or if the data attribute of the service data is an image type, the blockchain node determines the digest of the service data, and encrypts the digest by using the private key in the predetermined public-private key pair corresponding to the user identifier included in the service data. If the service data is the medical data, due to features such as decentralization, transparency, tamper resistance, and trustworthiness of the blockchain technology, different processing methods are used based on the data attribute of the medical data to store the medical data in the blockchain network, which can not only ensure authenticity of the medical data, but also ensure that the medical data is not tampered with, thereby maintaining integrity of the entire medical data. In addition, the medical data is effectively shared in the blockchain network.

BRIEF DESCRIPTION OF DRAWINGS

The accompanying drawings described here are intended to provide a further understanding of the present disclosure, and constitute a part of the present disclosure. The illustrative implementations of the present disclosure and descriptions thereof are intended to describe the present disclosure, and do not constitute limitations on the present disclosure. In the accompanying drawings.

DESCRIPTION OF IMPLEMENTATIONS

To make the objectives, technical solutions, and advantages of the present disclosure clearer, the following describes the technical solutions of the present disclosure with reference to specific implementations and accompanying drawings of the present disclosure. Apparently, the described implementations are merely some rather than all of the implementations of the present disclosure. All other implementations obtained by a person of ordinary skill in the art based on the implementations of the present disclosure without creative efforts shall fall within the protection scope of the present disclosure.

The technical solutions provided in the implementations of the present disclosure are described in detail below with reference to the accompanying drawings.

Figure 1:
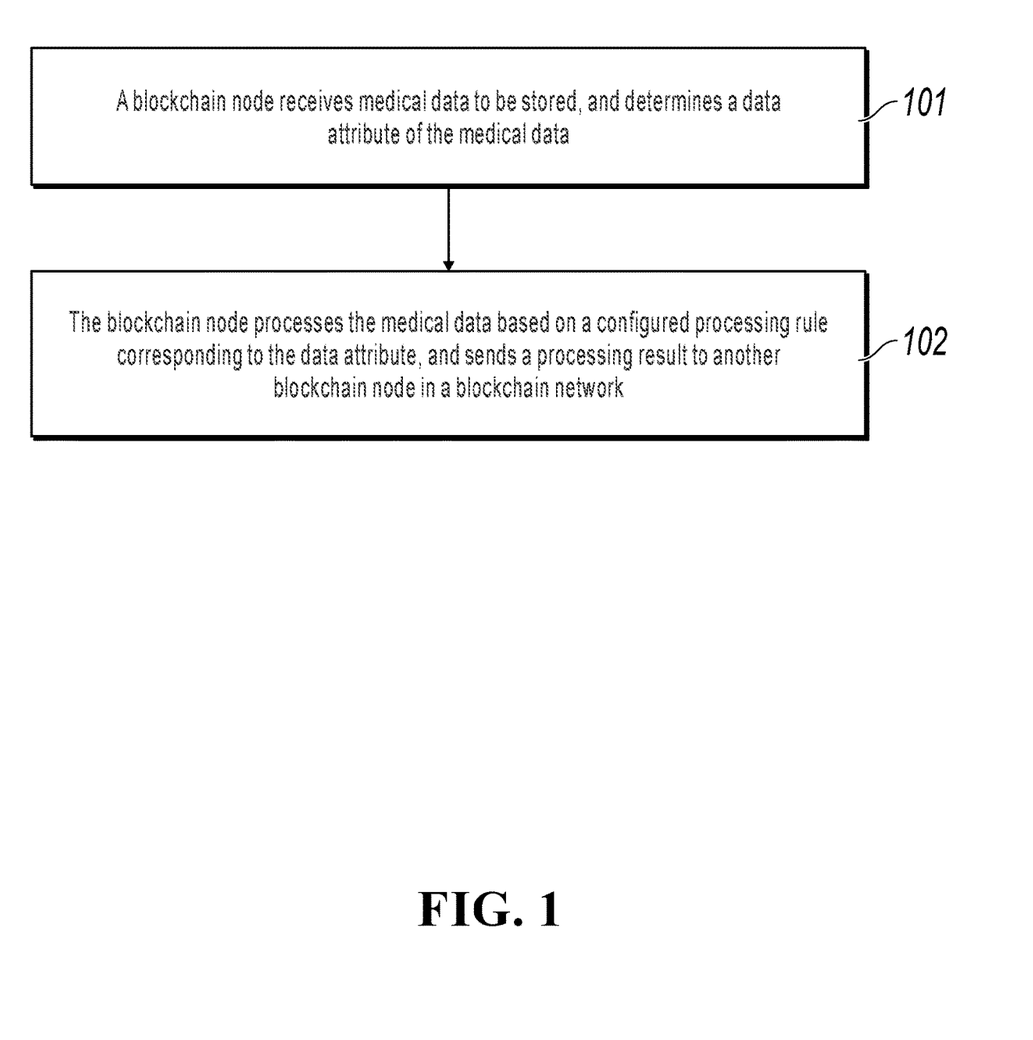
FIG. 1 is a schematic flowchart illustrating a blockchain-based data processing method, according to an implementation of the present disclosure.

FIG. 1 is a schematic flowchart illustrating a blockchain-based data processing method, according to an implementation of the present disclosure. The method can be described as follows. Service data described in this implementation of the present disclosure can be medical data. An example that the service data is the medical data is used below for detailed description.

In this implementation of the present disclosure, medical data management servers used in different medical institutions are separately used as blockchain nodes in a blockchain network, and a blockchain application used for medical data management is installed on each medical data management server. As such, medical data can be stored in the blockchain network based on the blockchain technology by using the blockchain application, to ensure that the medical data is authentic and is not tampered with, and that the medical data can be shared between different medical institutions.

Step 101: A blockchain node receives medical data to be stored, and determines a data attribute of the medical data.

In this implementation of the present disclosure, medical data is generated when a patient performs a medical activity in a medical institution. The medical data can be gathered in a medical information system of the medical institution, and therefore the medical data needs to be stored in the blockchain network in time. To be specific, the blockchain node can obtain the medical data to be stored from the medical information system in real time or periodically. The medical data can belong to one patient or a plurality of patients, which is not specifically limited here.

In practice, the medical data can be of a text type. For example, if a medical staff learns of a patient's condition through language communication with the patient, the medical staff can record the learned patient's condition in a literal form based on a patient's condition record specification, which can be referred to as a patient's condition record file. The patient's condition record file belongs to the medical data of a text type. The medical data can be of an image type. For example, when a patient visits a doctor in a medical institution, some physical examinations need to be performed on the patient, and these examinations are usually performed by specific devices. Most of examination data generated by these devices are referred to as medical image data, and the medical image data belongs to the medical data of an image type, for example, computed tomography (CT).

The blockchain node needs to further determine the data attribute of the medical data when receiving the medical data to be stored. The data attribute here includes but is not limited to a text type and an image type.

The blockchain node can determine the data attribute of the medical data based on a data format of the obtained medical data to be stored. For example, if the data format of the medical data is ".txt", the blockchain node can determine that the data attribute of the medical data is a text type. If the data format of the medical data is ".jpg", the blockchain node can determine that the data attribute of the medical data is an image type.

It is worthwhile to note that the medical data can be a digitized form of an electronic medical record of a patient. The electronic medical record is digitized information such as words, symbols, graphs, figures, data, and images that are generated by using a medical institution information system in a process that a medical staff performs a medical activity on the patient, and is a record form of a medical record of the patient. In addition to the electronic medical record of the patient, the medical data described in this implementation of the present disclosure includes identity information (for example, a height, a weight, an age, and a date of birth), body feature information (for example, a blood pressure, a blood type, and a heart rate), etc. of the patient.

Step 102: The blockchain node processes the medical data based on a configured processing rule corresponding to the data attribute, and sends a processing result to another blockchain node in a blockchain network.

Because the medical data of an image type occupies a relatively large capacity, data processing efficiency of the blockchain network is reduced if the medical data is transmitted in the blockchain network. Considering this case, in this implementation of the present disclosure, a processing rule matching medical data of different data attributes received by the blockchain node is configured, so as to improve efficiency of processing the medical data by the blockchain network.

It is worthwhile to note that medical data of different data attributes corresponds to different processing rules. The medical data of a text type can be stored in each blockchain node in the blockchain network. A processing method used for the medical data of an image type that occupies a relatively large capacity is to store the original medical data of an image type in a medical information database of a medical institution, and store a digest of the medical data in the blockchain network to prevent the medical data from being tampered with, which does not affect processing efficiency of the blockchain network, and can also ensure that the medical data is not tampered with, thereby maintaining authenticity and integrity of the medical data.

After determining the data attribute of the medical data, if the data attribute of the medical data is text type, the blockchain node encrypts the medical data by using a private key in a predetermined public-private key pair corresponding to a user identifier included in the medical data.

It is worthwhile to note that the blockchain network can predetermine a public-private key pair for each patient, and different patients have different private keys. As such, the blockchain node encrypts the medical data of the patient by using the private key of the patient, to ensure security of the medical data of the patient.

In this implementation of the present disclosure, because a capacity occupied by the medical data of a text type is not large, the medical data of a text type can be stored in the blockchain network.

Preferably, after broadcasting an encryption processing result to another blockchain node in the blockchain network, the blockchain node initiates consensus processing on the medical data, and stores the medical data to a blockchain if the consensus succeeds.

The blockchain node determines a check value of a first block including the user identifier based on the user identifier included in the medical data.

The blockchain node stores the check value and the medical data in a second block, and stores the second block in a blockchain where the first block is located.

It is worthwhile to note that the first block described in this implementation of the present disclosure can be understood as a block that recently stores the medical data of the patient. As such, based on the solution described in this implementation of the present disclosure, a medical record of the patient can be quickly traced, thereby helping a medical staff make an accurate diagnosis solution.

After determining the data attribute of the medical data, if the data attribute of the medical data is an image type, the blockchain node determines a digest of the medical data, and encrypts the digest by using a private key in a predetermined public-private key pair corresponding to a user identifier included in the medical data.

The medical data of an image type occupies a relatively large capacity. Therefore, when determining that the data attribute of the medical data is an image type, the blockchain node obtains the digest of the medical data through calculation by using a specified algorithm. Once the medical data is modified, it means that a digest of modified medical data is different from the digest of the original medical data. In this case, the blockchain node stores the digest in the blockchain network, which can also ensure that the medical data is not tampered with.

In addition, the blockchain node establishes a mapping relationship between the digest and a data identifier of the medical data, and stores the medical data in a medical information database based on the mapping relationship.

Therefore, it is convenient for another blockchain node to quickly find the medical data corresponding to the digest from a medical information database corresponding to the blockchain node when the another blockchain node needs the medical data.

In another implementation of the present disclosure, the method further includes: receiving, by the blockchain node, a medical data query request, where the medical data query request includes a digital signature of a user who initiates a query and a queried user identifier; authenticating, by the blockchain node, the user who initiates the query based on the digital signature; and sending, by the blockchain node, medical data corresponding to the queried user identifier to the user who initiates the query when the authentication succeeds.

Because the medical data relates to personal privacy of the patient, when a user queries the medical data of the patient, the user needs to be authenticated. The authentication here can include but is not limited to two aspects: whether the user is the patient and whether the user is a doctor of the patient.

The blockchain network can preconfigure public-private key pairs for medical staffs (for example, doctors and nurses) in different medical institutions. When a medical staff initiates a medical data query request, information about the medical staff can be encrypted by using a private key to obtain a digital signature of the medical staff. As such, when receiving the medical data query request, the blockchain node can authenticate the medical staff based on the data signature, to ensure security of the medical data.

The sending, by the blockchain node, medical data corresponding to the queried user identifier to the user who initiates the query includes: determining, by the blockchain node, a medical data access permission of the user who initiates the query; and selecting, by the blockchain node, medical data satisfying the access permission from the medical data corresponding to the queried user identifier, and sending the selected medical data to the user who initiates the query.

It is worthwhile to note that the blockchain network can set an access permission for the medical data. To be specific, even if the authentication succeeds, different query results can be obtained because users who initiate queries have different access permissions, which can effectively protect privacy of the patient.

The access permission here can be set based on different levels of the medical staffs, or can be set based on different query purposes, which is not specifically limited here.

Specifically, the sending, by the blockchain node, medical data corresponding to the queried user identifier to the user who initiates the query includes: if a data attribute of the queried medical data included in the medical data query request is an image type, determining, by the blockchain node, a digest of the queried medical data, and sending the digest to the medical information database; and receiving, by the blockchain node, medical data that corresponds to the digest and that is returned by the medical information database, verifying the received medical data based on the digest, and sending the received medical data to the user who initiates the query when the verification succeeds.

Through verification of the medical data, whether the medical data stored in the medical information database is tampered with can be discovered in time, and authenticity of a returned query result can also be ensured.

In the technical solution provided in this implementation of the present disclosure, after receiving the medical data to be stored, the blockchain node determines the data attribute of the medical data, processes the medical data based on the configured processing rule corresponding to the data attribute, and sends the processing result to another blockchain node in the blockchain network. In terms of medical data storage, due to features such as decentralization, transparency, tamper resistance, and trustworthiness of the blockchain technology, the medical data is processed by using different processing rules based on the data attribute of the medical data, to store the medical data in the blockchain network, which can not only ensure authenticity of the medical data, but also ensure that the medical data is not tampered with, thereby maintaining integrity of the entire medical data. In addition, the medical data is effectively shared in the blockchain network.

Figure 2:
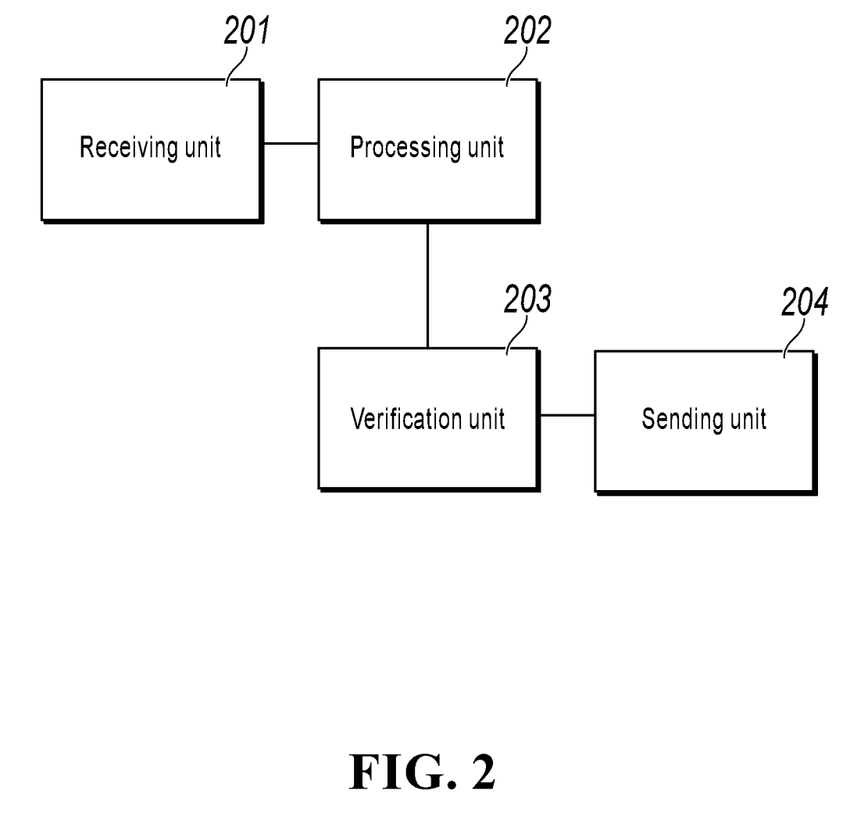
FIG. 2 is a schematic structural diagram illustrating a blockchain-based data processing device, according to an implementation of the present disclosure.

FIG. 2 is a schematic structural diagram illustrating a blockchain-based data processing device, according to an implementation of the present disclosure. The data processing device includes a receiving unit 201 and a processing unit 202.

The receiving unit 201 is configured to receive service data to be stored, and determine a data attribute of the service data.

The processing unit 202 is configured to process the service data based on a configured processing rule corresponding to the data attribute, and send a processing result to another blockchain node in a blockchain network.

In another implementation of the present disclosure, the service data is medical data.

In another implementation of the present disclosure, that the processing unit 202 processes the service data based on the configured processing rule corresponding to the data attribute includes: if the data attribute of the medical data is a text type, encrypting the medical data by using a private key in a predetermined public-private key pair corresponding to a user identifier included in the medical data.

In another implementation of the present disclosure, the processing unit 202 determines a check value of a first block including the user identifier based on the user identifier included in the medical data.

The processing unit 202 stores the check value and the medical data in a second block, and stores the second block in a blockchain where the first block is located.

In another implementation of the present disclosure, that the processing unit 202 processes the service data based on the configured processing rule corresponding to the data attribute includes: if the data attribute of the medical data is an image type, determining a digest of the medical data, and encrypting the digest by using a private key in a predetermined public-private key pair corresponding to a user identifier included in the medical data.

In another implementation of the present disclosure, the processing unit 202 establishes a mapping relationship between the digest and a data identifier of the medical data, and stores the medical data in a medical information database based on the mapping relationship.

In another implementation of the present disclosure, the processing device further includes a verification unit 203 and a sending unit 204.

The receiving unit 201 is configured to receive a medical data query request, where the medical data query request includes a digital signature of a user who initiates a query and a queried user identifier.

The verification unit 203 is configured to authenticate the user who initiates the query based on the digital signature.

The sending unit 204 is configured to send medical data corresponding to the queried user identifier to the user who initiates the query when the authentication succeeds.

In another implementation of the present disclosure, that the sending unit 204 sends the medical data corresponding to the queried user identifier to the user who initiates the query includes: determining a medical data access permission of the user who initiates the query; and selecting medical data satisfying the access permission from the medical data corresponding to the queried user identifier, and sending the selected medical data to the user who initiates the query.

In another implementation of the present disclosure, that the sending unit 204 sends the medical data corresponding to the queried user identifier to the user who initiates the query includes: if a data attribute of the queried medical data included in the medical data query request is an image type, determining a digest of the queried medical data, and sending the digest to the medical information database; and receiving medical data that corresponds to the digest and that is returned by the medical information database, verifying the received medical data based on the digest, and sending the received medical data to the user who initiates the query when the verification succeeds.

It is worthwhile to note that the processing device provided in this implementation of the present disclosure can be implemented by using software or hardware, which is not specifically limited here. After receiving the medical data to be stored, the processing device determines the data attribute of the medical data, processes the medical data based on the configured processing rule corresponding to the data attribute, and sends the processing result to another blockchain node in the blockchain network. In terms of medical data storage, due to features such as decentralization, transparency, tamper resistance, and trustworthiness of the blockchain technology, the medical data is processed by using different processing rules based on the data attribute of the medical data, to store the medical data in the blockchain network, which can not only ensure authenticity of the medical data, but also ensure that the medical data is not tampered with, thereby maintaining integrity of the entire medical data. In addition, the medical data is effectively shared in the blockchain network.

Figure 3:
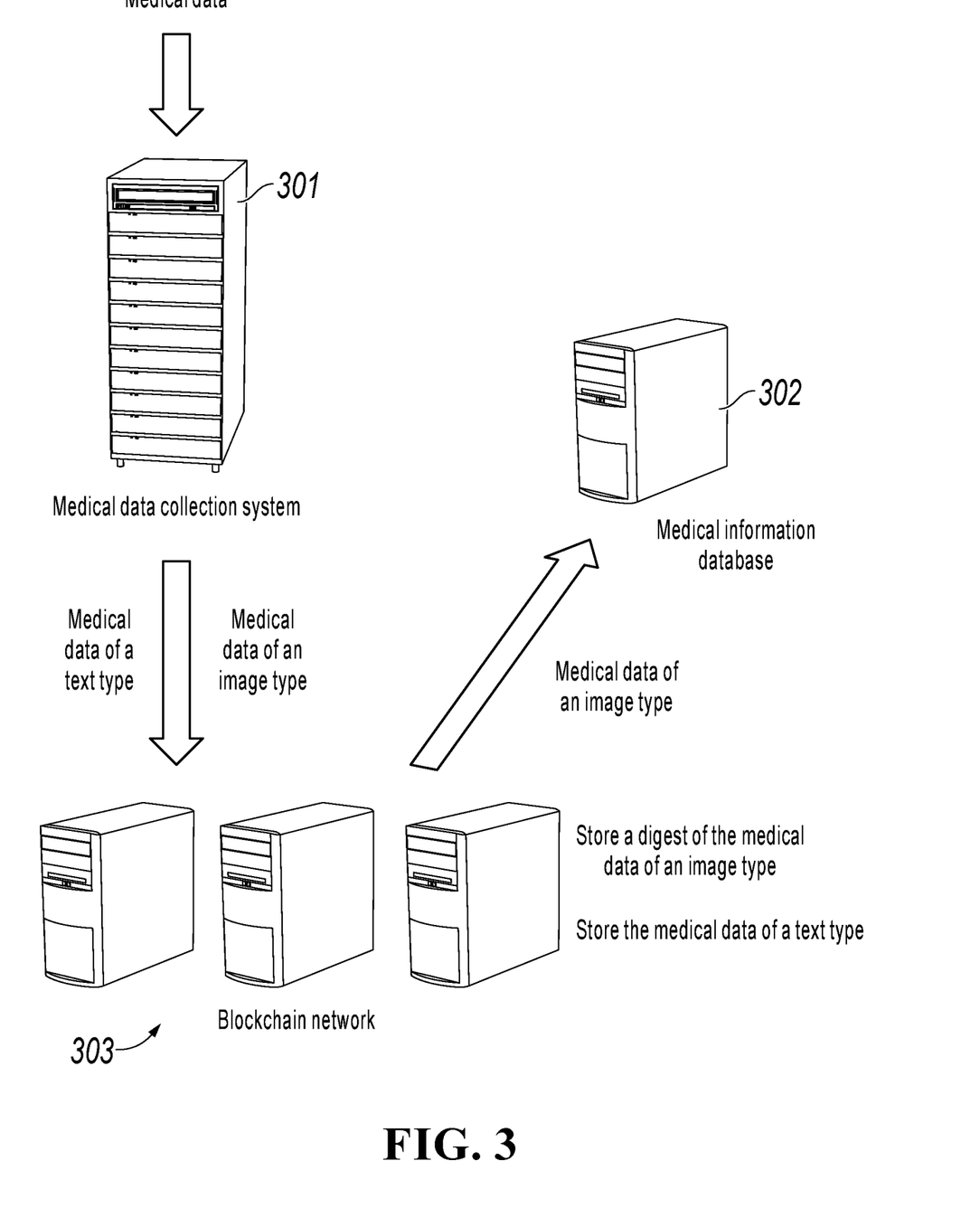
FIG. 3 is a schematic structural diagram illustrating a blockchain-based medical data processing system, according to an implementation of the present disclosure.

FIG. 3 is a schematic structural diagram illustrating a blockchain-based medical data processing system, according to an implementation of the present disclosure. The medical data processing system includes a medical data collection system 301, a medical information database 302, and a blockchain network 303.

The medical data collection system 301 collects medical data of a patient through various medical device interfaces. The medical data here includes medical data in a text form (for example, patient's condition record data) and medical data in an image form (for example, medical image data).

A blockchain node in the blockchain network 303 receives medical data to be stored from the medical data collection system 301, determines a data attribute of the medical data; and if the data attribute of the medical data is a text type, the blockchain node encrypts the medical data by using a private key in a predetermined public-private key pair corresponding to a user identifier included in the medical data; or if the data attribute of the medical data is an image type, the blockchain node determines a digest of the medical data, and encrypts the digest by using a private key in a predetermined public-private key pair corresponding to a user identifier included in the medical data.

For the medical data of a text type, the blockchain node in the blockchain network 303 determines a check value of a first block including the user identifier based on the user identifier included in the medical data.

The blockchain node stores the check value and the medical data in a second block, and stores the second block in a blockchain where the first block is located.

For the medical data of an image type, the blockchain node in the blockchain network 303 establishes a mapping relationship between the digest and a data identifier of the medical data, and stores the medical data in the medical information database 302 based on the mapping relationship.

The blockchain node in the blockchain network 303 receives a medical data query request, where the medical data query request includes a digital signature of a user who initiates a query and a queried user identifier.

The blockchain node authenticates the user who initiates the query based on the digital signature.

The blockchain node sends medical data corresponding to the queried user identifier to the user who initiates the query when the authentication succeeds.

That the blockchain node in the blockchain network 303 sends the medical data corresponding to the queried user identifier to the user who initiates the query includes: determining a medical data access permission of the user who initiates the query; and selecting medical data satisfying the access permission from the medical data corresponding to the queried user identifier, and sending the selected medical data to the user who initiates the query.

That the blockchain node in the blockchain network 303 sends the medical data corresponding to the queried user identifier to the user who initiates the query includes: if a data attribute of the queried medical data included in the medical data query request is an image type, determining, by the blockchain node, a digest of the queried medical data, and sending the digest to the medical information database; and receiving medical data that corresponds to the digest and that is returned by the medical information database, verifying the received medical data based on the digest, and sending the received medical data to the user who initiates the query when the verification succeeds.

Figure 4:
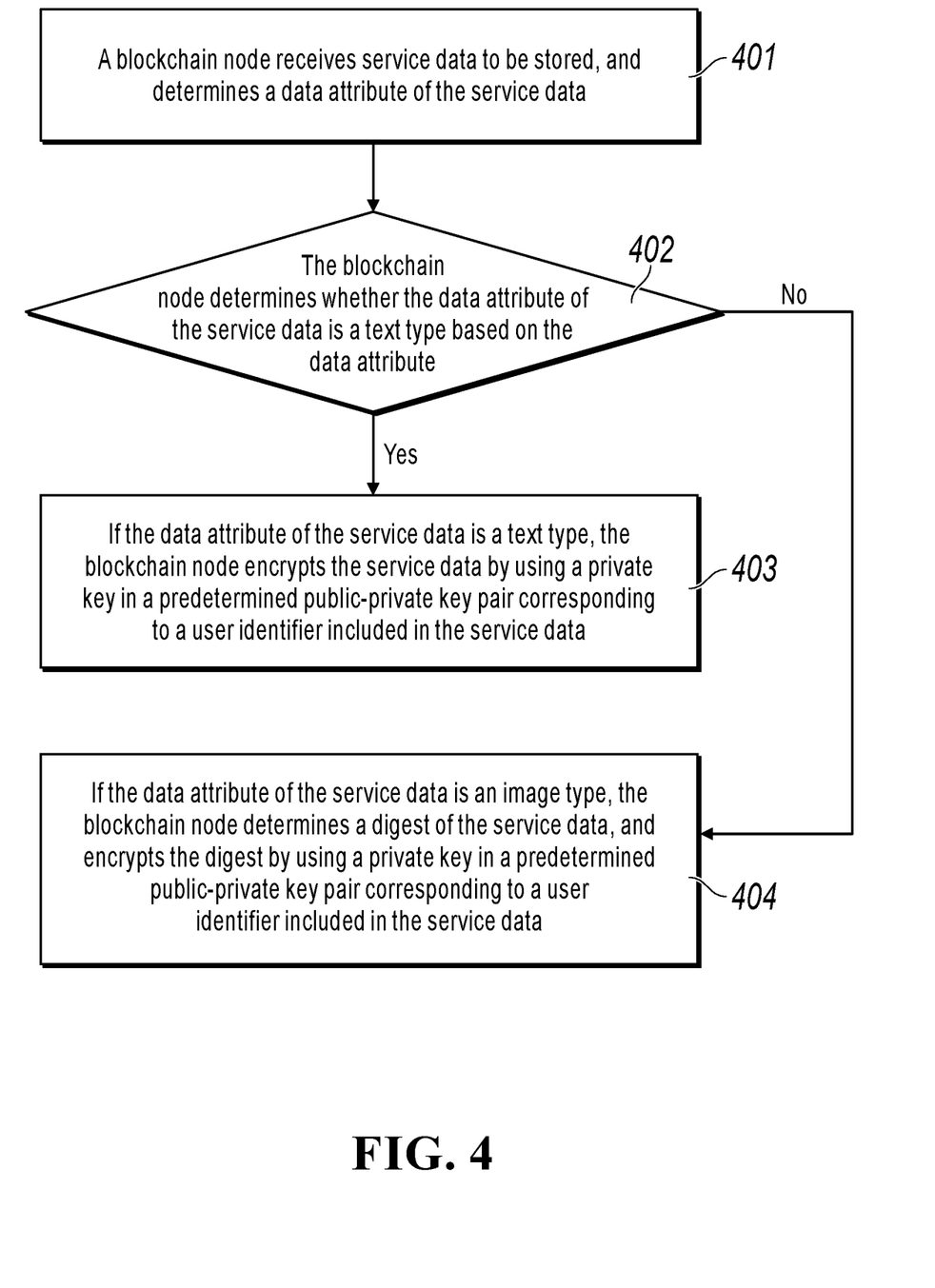
FIG. 4 is a schematic flowchart illustrating a blockchain-based data processing method, according to an implementation of the present disclosure.

FIG. 4 is a schematic flowchart illustrating a blockchain-based data processing method, according to an implementation of the present disclosure. The method can be described as follows.

Step 401: A blockchain node receives service data to be stored, and determines a data attribute of the service data.

In this implementation of the present disclosure, the service data to be stored can be medical data or service data of another service, which is not limited here.

Step 402: The blockchain node performs step 403 if the blockchain node determines that the data attribute of the service data is a text type based on the data attribute; or the blockchain node performs step 404 if the blockchain node determines that the data attribute of the service data is an image type.

Step 403: If the data attribute of the service data is a text type, the blockchain node encrypts the service data by using a private key in a predetermined public-private key pair corresponding to a user identifier included in the service data.

Preferably, after broadcasting an encryption processing result to another blockchain node in a blockchain network, the blockchain node initiates consensus processing on the service data, and stores the service data to a blockchain if the consensus succeeds.

The blockchain node determines a check value of a first block including the user identifier based on the user identifier included in the service data.

The blockchain node stores the check value and the service data in a second block, and stores the second block in a blockchain where the first block is located.

Step 404: If the data attribute of the service data is an image type, the blockchain node determines a digest of the service data, and encrypts the digest by using a private key in a predetermined public-private key pair corresponding to a user identifier included in the service data.

Because the service data of an image type occupies a relatively large capacity, when determining that the data attribute of the service data is an image type, the blockchain node obtains the digest of the service data through calculation by using a specified algorithm.

After broadcasting the digest to another blockchain node in the blockchain network, the blockchain node initiates consensus processing on the service data, and stores the digest of the service data to a blockchain if the consensus succeeds.

Once the service data is modified, it means that a digest of modified service data is different from the digest of the original service data. In this case, the digest is stored in the blockchain network, so as to ensure that the service data is not tampered with.

In addition, the blockchain node establishes a mapping relationship between the digest and a data identifier of the service data, and stores the service data in a service database based on the mapping relationship.

Therefore, it is convenient for another blockchain node to quickly find the service data corresponding to the digest from the service database corresponding to the blockchain node when the blockchain node needs the service data.

Preferably, the method further includes: receiving, by the blockchain node, a service data query request, where the service data query request includes a digital signature of a user who initiates a query and a queried user identifier; authenticating, by the blockchain node, the user who initiates the query based on the digital signature; and sending, by the blockchain node, service data corresponding to the queried user identifier to the user who initiates the query when the authentication succeeds.

Preferably, the sending, by the blockchain node, service data corresponding to the queried user identifier to the user who initiates the query includes: determining, by the blockchain node, a service data access permission of the user who initiates the query; and selecting, by the blockchain node, service data satisfying the access permission from the service data corresponding to the queried user identifier, and sending the selected service data to the user who initiates the query.

Preferably, the sending, by the blockchain node, service data corresponding to the queried user identifier to the user who initiates the query includes: if a data attribute of the queried service data included in the service data query request is an image type, determining, by the blockchain node, a digest of the queried service data, and sending the digest to the service database; and receiving, by the blockchain node, service data that corresponds to the digest and that is returned by the service database, verifying the received service data based on the digest, and sending the received service data to the user who initiates the query when the verification succeeds.

In the technical solution provided in this implementation of the present disclosure, due to features such as decentralization, transparency, tamper resistance, and trustworthiness of the blockchain technology, different processing methods are used based on the data attribute of the service data to store the service data in the blockchain network, which can not only ensure authenticity of the service data, but also ensure that the service data is not tampered with, thereby maintaining integrity of the entire service data. In addition, the service data is effectively shared in the blockchain network.

Figure 5:
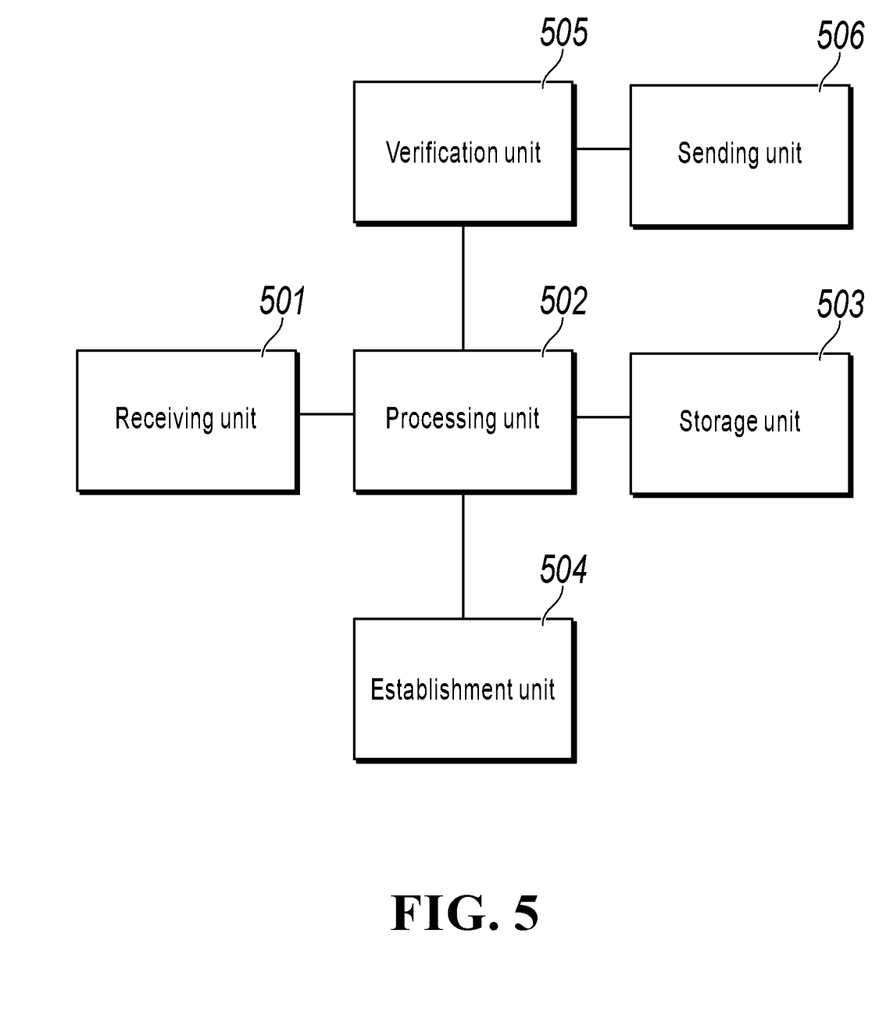
FIG. 5 is a schematic structural diagram illustrating a blockchain-based data processing device, according to an implementation of the present disclosure.

FIG. 5 is a schematic structural diagram illustrating a blockchain-based data processing device, according to an implementation of the present disclosure. The data processing device includes a receiving unit 501 and a processing unit 502.

The receiving unit 501 is configured to receive service data to be stored, and determine a data attribute of the service data.

The processing unit 502 is configured to: if the data attribute of the service data is a text type, encrypt the service data by using a private key in a predetermined public-private key pair corresponding to a user identifier included in the service data; or if the data attribute of the service data is an image type, determine a digest of the service data, and encrypt the digest by using a private key in a predetermined public-private key pair corresponding to a user identifier included in the service data.

In another implementation of the present disclosure, the data processing device further includes a storage unit 503.

The storage unit 503 is configured to: if the data attribute of the service data is a text type, determine a check value of a first block including the user identifier based on the user identifier included in the service data; and store the check value and the service data in a second block, and store the second block in a blockchain where the first block is located.

In another implementation of the present disclosure, the data processing device further includes an establishment unit 504.

The establishment unit 504 is configured to: if the data attribute of the service data is an image type, establish a mapping relationship between the digest and a data identifier of the service data, and store the service data in a service database based on the mapping relationship.

In another implementation of the present disclosure, the data processing device further includes a verification unit 505 and a sending unit 506.

The receiving unit 501 is configured to receive a service data query request, where the service data query request includes a digital signature of a user who initiates a query and a queried user identifier.

The verification unit 505 is configured to authenticate the user who initiates the query based on the digital signature.

The sending unit 506 is configured to send service data corresponding to the queried user identifier to the user who initiates the query when the authentication succeeds.

In another implementation of the present disclosure, that the sending unit 506 sends the service data corresponding to the queried user identifier to the user who initiates the query includes: determining a service data access permission of the user who initiates the query; and selecting service data satisfying the access permission from the service data corresponding to the queried user identifier, and sending the selected service data to the user who initiates the query.

In another implementation of the present disclosure, that the sending unit 506 sends the service data corresponding to the queried user identifier to the user who initiates the query includes: if a data attribute of the queried service data included in the service data query request is an image type, determining a digest of the queried service data, and sending the digest to the service database; and receiving service data that corresponds to the digest and that is returned by the service database, verifying the received service data based on the digest, and sending the received service data to the user who initiates the query when the verification succeeds.

It is worthwhile to note that the data processing device provided in this implementation of the present disclosure can be implemented by using software or hardware, which is not specifically limited here. Due to features such as decentralization, transparency, tamper resistance, and trustworthiness of the blockchain technology, the data processing device uses different processing methods based on the data attribute of the service data to store the service data in a blockchain network, which can not only ensure authenticity of the service data, but also ensure that the service data is not tampered with, thereby maintaining integrity of the entire service data. In addition, the service data is effectively shared in the blockchain network.

In the 1990s, whether a technical improvement is a hardware improvement (for example, an improvement to a circuit structure such as a diode, a transistor, or a switch) or a software improvement (an improvement to a method procedure) can be clearly distinguished. However, as technologies develop, current improvements to many method procedures can be considered as direct improvements to hardware circuit structures. A designer usually programs an improved method procedure into a hardware circuit, to obtain a corresponding hardware circuit structure. Therefore, a method procedure can be improved by using a hardware entity module. For example, a programmable logic device (PLD) (for example, a field programmable gate array (FPGA)) is such an integrated circuit, and a logical function of the PLD is determined by a user through device programming. The designer performs programming to "integrate" a digital system to a PLD without requesting a chip manufacturer to design and produce an application-specific integrated circuit chip. In addition, at present, instead of manually manufacturing an integrated circuit chip, such programming is mostly implemented by using "logic compiler" software. The logic compiler software is similar to a software compiler used to develop and write a program. Original code needs to be written in a particular programming language for compilation. The language is referred to as a hardware description language (HDL). There are many HDLs, such as Advanced Boolean Expression Language (ABEL), Altera Hardware Description Language (AHDL), Confluence, Cornell University Programming Language (CUPL), HDCal, Java Hardware Description Language (JHDL), Lava, Lola, MyHDL, PALASM, and Ruby Hardware Description Language (RHDL). The very-high-speed integrated circuit hardware description language (VHDL) and Verilog are most commonly used. A person skilled in the art should also understand that a hardware circuit that implements a logical method procedure can be readily obtained once the method procedure is logically programmed by using the several described hardware description languages and is programmed into an integrated circuit.

A controller can be implemented by using any appropriate method. For example, the controller can be a microprocessor or a processor, or a computer-readable medium that stores computer readable program code (such as software or firmware) that can be executed by the microprocessor or the processor, a logic gate, a switch, an application-specific integrated circuit (ASIC), a programmable logic controller, or a built-in microprocessor. Examples of the controller include but are not limited to the following microprocessors: ARC 625D, Atmel AT91SAM, Microchip PIC18F26K20, and Silicone Labs C8051F320. The memory controller can also be implemented as a part of the control logic of the memory. A person skilled in the art also knows that in addition to implementing the controller by using the computer readable program code, logic programming can be performed on method steps to allow the controller to implement the same function in forms of the logic gate, the switch, the application-specific integrated circuit, the programmable logic controller, and the built-in microcontroller. Therefore, the controller can be considered as a hardware component, and an apparatus configured to implement various functions in the controller can also be considered as a structure in the hardware component; or the apparatus configured to implement various functions can even be considered as both a software module implementing the method and a structure in the hardware component.

The system, apparatus, module, or unit illustrated in the previous implementations can be implemented by using a computer chip or an entity or can be implemented by using a product having a certain function. A typical implementation device is a computer. The computer can be, for example, a personal computer, a laptop computer, a cellular phone, a camera phone, a smartphone, a personal digital assistant, a media player, a navigation device, an email device, a game console, a tablet computer, a wearable device, or any combination of these devices.

For ease of description, the above apparatus is described by dividing functions into various units. Certainly, when the present disclosure is implemented, a function of each unit can be implemented in one or more pieces of software and/or hardware.

A person skilled in the art should understand that an implementation of the present disclosure can be provided as a method, a system, or a computer program product. Therefore, the present disclosure can use a form of hardware only implementations, software only implementations, or implementations with a combination of software and hardware. Moreover, the present disclosure can use a form of a computer program product that is implemented on one or more computer-usable storage media (including but not limited to a disk memory, a CD-ROM, an optical memory, etc.) that include computer-usable program code.

The present disclosure is described with reference to the flowcharts and/or block diagrams of the method, the device (system), and the computer program product based on the implementations of the present disclosure. It is worthwhile to note that computer program instructions can be used to implement each process and/or each block in the flowcharts and/or the block diagrams and a combination of a process and/or a block in the flowcharts and/or the block diagrams. These computer program instructions can be provided for a general-purpose computer, a dedicated computer, an embedded processor, or a processor of another programmable data processing device to generate a machine, so that the instructions executed by the computer or the processor of the another programmable data processing device generate an apparatus for implementing a specific function in one or more processes in the flowcharts and/or in one or more blocks in the block diagrams.

These computer program instructions can be stored in a computer readable memory that can instruct the computer or the another programmable data processing device to work in a specific way, so that the instructions stored in the computer readable memory generate an artifact that includes an instruction apparatus. The instruction apparatus implements a specific function in one or more processes in the flowcharts and/or in one or more blocks in the block diagrams.

These computer program instructions can be loaded onto the computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

In a typical configuration, a computing includes one or more processors (CPU), one or more input/output interfaces, one or more network interfaces, and one or more memories.

The memory can include a non-persistent memory, a random access memory (RAM), a non-volatile memory, and/or another form that are in a computer readable medium, for example, a read-only memory (ROM) or a flash memory (flash RAM). The memory is an example of the computer readable medium.

The computer readable medium includes persistent, non-persistent, movable, and unmovable media that can store information by using any method or technology. The information can be a computer readable instruction, a data structure, a program module, or other data. Examples of a computer storage medium include but are not limited to a parameter random access memory (PRAM), a static random access memory (SRAM), a dynamic random access memory (DRAM), another type of random access memory (RAM), a read-only memory (ROM), an electrically erasable programmable read-only memory (EEPROM), a flash memory or another memory technology, a compact disc read-only memory (CD-ROM), a digital versatile disc (DVD) or another optical storage, a cassette magnetic tape, a magnetic tape/magnetic disk storage or another magnetic storage device, or any other non-transmission medium. The computer storage medium can be used to store information accessible by the computing. Based on the definition in the present specification, the computer readable medium does not include transitory computer readable media (transitory media) such as a modulated data signal and carrier.

It is worthwhile to further note that the terms "include", "comprise", or their any other variants are intended to cover a non-exclusive inclusion, so that a process, method, product or device that includes a list of elements not only includes those elements but also includes other elements not expressly listed, or further includes elements inherent to such process, method, product or device. Without more constraints, an element preceded by "includes a . . . " does not preclude the existence of additional identical elements in the process, method, product or device that includes the element.

The present disclosure can be described in the general context of computer executable instructions executed by a computer, for example, a program module. Generally, the program module includes a routine, a program, an object, a component, a data structure, etc. executing a specific task or implementing a specific abstract data type. The present disclosure can also be practiced in distributed computing environments. In the distributed computing environments, tasks are performed by remote processing devices connected through a communications network. In a distributed computing environment, the program module can be located in both local and remote computer storage media including storage devices.

The implementations in the present specification are described in a progressive way. For same or similar parts of the implementations, references can be made to the implementations. Each implementation focuses on a difference from other implementations. Particularly, a system implementation is basically similar to a method implementation, and therefore is described briefly. For related parts, reference can be made to related descriptions in the method implementation.

The previous implementations are implementations of the present disclosure, and are not intended to limit the present disclosure. A person skilled in the art can make various modifications and changes to the present disclosure. Any modification, equivalent replacement, or improvement made without departing from the spirit and principle of the present disclosure shall fall within the scope of the claims in the present disclosure.

Figure 6:
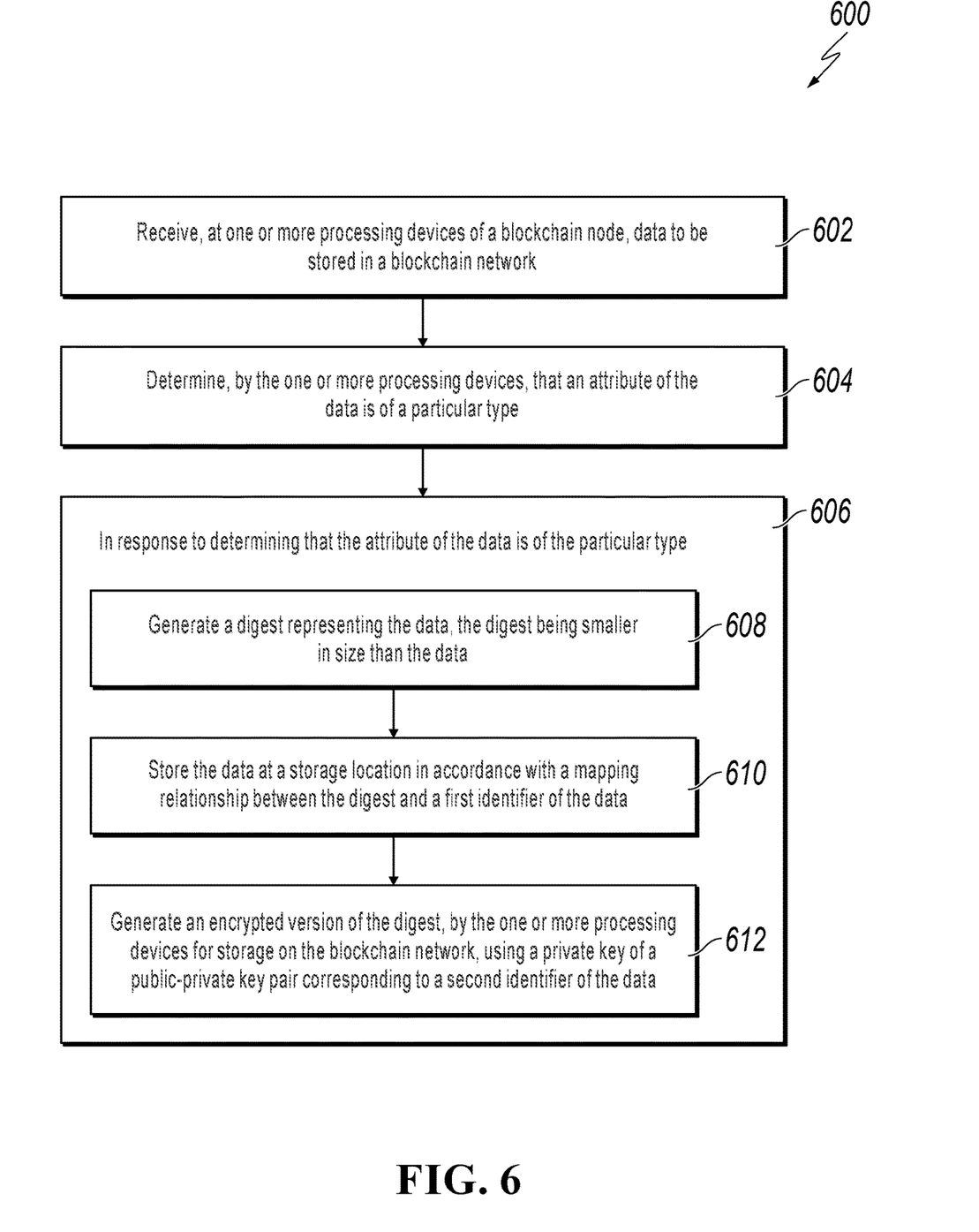
FIG. 6 is a flowchart illustrating an example of a computer-implemented method for processing data in a blockchain network, according to an implementation of the present disclosure.

FIG. 6 is a flowchart illustrating an example of a computer-implemented method 600 for processing data in a blockchain network, according to an implementation of the present disclosure. For clarity of presentation, the description that follows generally describes method 600 in the context of the other figures in this description. However, it will be understood that method 600 can be automatically performed, for example, by other combinations of software and/or hardware modules in a distributed computing system. In some implementations, various steps of method 600 can be run in parallel, in combination, in loops, or in any order.

At 602, data to be stored in a blockchain network is received at one or more processing devices of a blockchain node. In some implementations, the data can be medical data (e.g., medical record of one or more patients). For example, electronic medical record of a patient can be stored in the blockchain network after a doctor visit. In some implementations, the blockchain node can be a server of a doctor's office or a server of a hospital, and the blockchain network can include multiple blockchain nodes. In some implementations, the data can be automatically stored in real time once the data has been created or modified. In some implementations, the data can be automatically stored periodically.

At 604, the one or more processing devices can be configured to determine that an attribute of the data is of a particular type. In some implementations, the particular type can include text and image. For example, writings by a doctor can be saved in a text format (e.g., .txt). Medical examination results (e.g., Computed Tomography (CT) results) can be saved in an image format (e.g., jpg). In some implementations, determining that an attribute of the data is of a particular type can include determining that an attribute of the data is of a text type or an image type. In some implementations, the one or more processing devices can process the data based on a processing rule corresponding to the particular type. In some implementations, other data attributes (e.g., size) can be determined, and used to select a processing rule to process the data.

At 606, in response to determining that the attribute of the data is of the particular type, steps 608, 610, and 612 are automatically performed. At 608, a digest representing the data is generated. For example, the one or more processing devices can calculate the digest based on the data using a predetermined rule. The digest is smaller in size than the underlying data that it represents. At 610, the data is stored at a storage location in accordance with a mapping relationship between the digest and a first identifier of the data. In some implementations, the first identifier is a data identifier, and can be used to identify the data. At 612, an encrypted version of the digest is generated, by the one or more processing devices for storage on the blockchain network, using a private key of a public-private key pair corresponding to a second identifier of the data. In some implementations, the second identifier is a user identifier, and can be used to identify a user of the data.

In some implementations, if the particular type is a text type, the one or more processing devices can determine a check value of a first block comprising the second identifier of the data. The one or more processing devices then can store both the check value and the data in a second block. The one or more processing devices then can store the second block in a blockchain where the first block is located.

In some implementations, if the particular type is an image type, the one or more processing devices can establish the mapping relationship between the digest and the first identifier of the data. The one or more processing devices then can store the data in a database based on the mapping relationship. For example, instead of storing large files (e.g., image files representing medical images) in the blockchain network, only the digests generated from such large files can be stored in the blockchain. The original image files can be stored in a local database (e.g., not in the blockchain network), but linked to the digest stored on the blockchain network. In some implementations, this allows for leveraging a blockchain network for securing large data files, without storing the large data file itself on the blockchain network.

In some implementations, a data query request can be received by the one or more processing devices. The data query request can include at least one of a digital signature of a user who initiates a query and a queried user identifier. The user who initiates the query can be authenticated by the one or more processing devices based on the digital signature. When the authentication succeeds, the one or more processing devices can send data corresponding to the queried user identifier to the user who initiates the query. For example, the one or more processing devices can determine a data access permission of the user who initiates the query. The one or more processing devices then can select data satisfying the data access permission from the data corresponding to the queried user identifier. The one or more processing devices then can send the data satisfying the data access permission to the user who initiates the query.

In some implementations, the one or more processing devices can determine a digest of the queried data. The one or more processing devices can send the digest of the queried data to a database, and receive, from the database, data that corresponds to the digest of the queried data. The one or more processing devices can verify the data received from the database based on the digest of the queried data. When the verification succeeds, the one or more processing devices can send the data received from the database to the user who initiates the query.

In some implementations, the one or more processing devices can process the data based on a processing rule corresponding to the particular type of data. The one or more processing devices can then send a processing result to other blockchain nodes in the blockchain network.

In some implementations, the one or more processing devices can determine a data size of the data. The one or more processing devices then can determine a storage location for the data based on the data size. For example, if the data size is smaller than a predetermined threshold, the data can be stored in the blockchain network. However, if the data size is larger than or equal to the predetermined threshold, the data can be stored in a local database rather than in the blockchain network, while a digest of the data is stored in the blockchain network.

The technology described herein can be applied for various forms of data, including, for example, medical data. While medical data of a patient can be stored and managed by a medical institution, it may be difficult in some cases to share medical data securely between different medical institutions. The subject matter described in this specification provides an efficient, effective, and secure data processing and storing method based on blockchain technology. Because storing large data files (e.g., medical images) directly in a blockchain network can be challenging due to the underlying computational burden, various medical data can be processed and stored differently based on a data type of the underlying files. For example, while small files (e.g., text files) are stored directly in a blockchain network, relatively larger files (e.g., large medical images) are stored in a local database, while reduced-sized digests generated from such large files are stored in the blockchain. As a result, large-size data can be securely stored by leveraging blockchain technology, while avoiding the computational burden associated with storing such large-size data directly in the blockchain network. The reduced-sized digest can provide efficient encryption, and a one-to-one mapping between the digest and the storage location of the data ensures easy retrieval once a query is authenticated.

Embodiments and the operations described in this specification can be implemented in digital electronic circuitry, or in computer software, firmware, or hardware, including the structures disclosed in this specification or in combinations of one or more of them. The operations can be implemented as operations performed by a data processing apparatus on data stored on one or more computer-readable storage devices or received from other sources. A data processing apparatus, computer, or computing device may encompass apparatus, devices, and machines for processing data, including by way of example a programmable processor, a computer, a system on a chip, or multiple ones, or combinations, of the foregoing. The apparatus can include special purpose logic circuitry, for example, a central processing unit (CPU), a field programmable gate array (FPGA) or an application-specific integrated circuit (ASIC). The apparatus can also include code that creates an execution environment for the computer program in question, for example, code that constitutes processor firmware, a protocol stack, a database management system, an operating system (for example an operating system or a combination of operating systems), a cross-platform runtime environment, a virtual machine, or a combination of one or more of them. The apparatus and execution environment can realize various different computing model infrastructures, such as web services, distributed computing and grid computing infrastructures.

A computer program (also known, for example, as a program, software, software application, software module, software unit, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be executed on one computer or on multiple computers that are located at one site or distributed across multiple sites and interconnected by a communication network.

Processors for execution of a computer program include, by way of example, both general- and special-purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data. A computer can be embedded in another device, for example, a mobile device, a personal digital assistant (PDA), a game console, a Global Positioning System (GPS) receiver, or a portable storage device. Devices suitable for storing computer program instructions and data include non-volatile memory, media and memory devices, including, by way of example, semiconductor memory devices, magnetic disks, and magneto-optical disks. The processor and the memory can be supplemented by, or incorporated in, special-purpose logic circuitry.

Mobile devices can include handsets, user equipment (UE), mobile telephones (for example, smartphones), tablets, wearable devices (for example, smart watches and smart eyeglasses), implanted devices within the human body (for example, biosensors, cochlear implants), or other types of mobile devices. The mobile devices can communicate wirelessly (for example, using radio frequency (RF) signals) to various communication networks (described below). The mobile devices can include sensors for determining characteristics of the mobile device's current environment. The sensors can include cameras, microphones, proximity sensors, GPS sensors, motion sensors, accelerometers, ambient light sensors, moisture sensors, gyroscopes, compasses, barometers, fingerprint sensors, facial recognition systems, RF sensors (for example, Wi-Fi and cellular radios), thermal sensors, or other types of sensors. For example, the cameras can include a forward- or rear-facing camera with movable or fixed lenses, a flash, an image sensor, and an image processor. The camera can be a megapixel camera capable of capturing details for facial and/or iris recognition. The camera along with a data processor and authentication information stored in memory or accessed remotely can form a facial recognition system. The facial recognition system or one-or-more sensors, for example, microphones, motion sensors, accelerometers, GPS sensors, or RF sensors, can be used for user authentication.

To provide for interaction with a user, embodiments can be implemented on a computer having a display device and an input device, for example, a liquid crystal display (LCD) or organic light-emitting diode (OLED)/virtual-reality (VR)/augmented-reality (AR) display for displaying information to the user and a touchscreen, keyboard, and a pointing device by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments can be implemented using computing devices interconnected by any form or medium of wireline or wireless digital data communication (or combination thereof), for example, a communication network. Examples of interconnected devices are a client and a server generally remote from each other that typically interact through a communication network. A client, for example, a mobile device, can carry out transactions itself, with a server, or through a server, for example, performing buy, sell, pay, give, send, or loan transactions, or authorizing the same. Such transactions may be in real time such that an action and a response are temporally proximate; for example an individual perceives the action and the response occurring substantially simultaneously, the time difference for a response following the individual's action is less than 1 millisecond (ms) or less than 1 second (s), or the response is without intentional delay taking into account processing limitations of the system.

Examples of communication networks include a local area network (LAN), a radio access network (RAN), a metropolitan area network (MAN), and a wide area network (WAN). The communication network can include all or a portion of the Internet, another communication network, or a combination of communication networks. Information can be transmitted on the communication network according to various protocols and standards, including Long Term Evolution (LTE), 5G, IEEE 802, Internet Protocol (IP), or other protocols or combinations of protocols. The communication network can transmit voice, video, biometric, or authentication data, or other information between the connected computing devices.

Features described as separate implementations may be implemented, in combination, in a single implementation, while features described as a single implementation may be implemented in multiple implementations, separately, or in any suitable sub-combination. Operations described and claimed in a particular order should not be understood as requiring that the particular order, nor that all illustrated operations must be performed (some operations can be optional). As appropriate, multitasking or parallel-processing (or a combination of multitasking and parallel-processing) can be performed.

What is claimed is:

1. A computer-implemented method for processing data in a blockchain network by one or more processing devices implementing blockchain nodes of the blockchain network, the method comprising:
   receiving, at a blockchain node of the blockchain network, a first data record to be stored in a blockchain maintained by the blockchain network, wherein the first data record is medical data generated in association with a first medical practitioner of a first medical institution, wherein the blockchain network comprises a plurality of blockchain nodes that respectively belong to a plurality of different medical institutions;
   preconfiguring a plurality of respective public-private key pairs for a plurality of medical practitioners employed by respective medical institutions of the plurality of the different medical institutions;
   determining that the first data record comprises textual data;
   in response to determining that the first data record comprises textual data, storing the textual data in the blockchain;
   receiving, at the blockchain node of the blockchain network, a second data record to be stored in the blockchain, wherein the second data record is medical data generated in association with the first medical practitioner of the first medical institution;
   determining that the second data record comprises non-textual data; and
   in response to determining that the second data record comprises non-textual data:
      generating a digest representing the non-textual data, wherein the digest is smaller in size than the non-textual data;
      establishing a mapping relationship between the digest and a data identifier of the non-textual data;
      storing the non-textual data at a database in accordance with the mapping relationship, wherein records of the database are not stored on the blockchain;
      generating an encrypted version of the digest using a user-specific key of a public-private key pair corresponding to a user identifier of the non-textual data;
      storing the encrypted version of the digest in the blockchain;
      generating, for a second medical practitioner of a different second medical institution, a digital signature for the second medical practitioner to access non-textual patient data generated by a plurality of different medical institutions maintaining blockchain nodes of the blockchain network, including encrypting information associated with the second medical practitioner using a private key of the second medical practitioner;
      receiving, from the second medical practitioner of the different second medical institution, a data query request for the second medical practitioner of the different second medical institution to access the non-textual data generated by the first medical institution, wherein the data query request includes the digital signature of the second medical practitioner and a queried user identifier;
      authenticating the second medical practitioner based on the digital signature of the second medical practitioner;
      determining a data access permission of the second medical practitioner, wherein the data access permission is determined based on a medical staff level of the second medical practitioner;
      determining, based on the data access permission, that the second medical practitioner is authorized to access the non-textual data associated with the data query request;
      in response, determining the digest of the non-textual data associated with the data query request;
      sending the digest of the non-textual data to the database;
      receiving the non-textual data that corresponds to the digest of the non-textual data and that is returned by the database;
      verifying the non-textual data received from the database based on the digest of the non-textual data;
      in response to a successful verification, selecting a query result satisfying the data access permission from the non-textual data corresponding to the queried user identifier; and
      sending the query result satisfying the data access permission to the second medical practitioner.

2. The computer-implemented method of claim 1, wherein storing the textual data in the blockchain comprises:
   determining a check value of a first block comprising the user identifier of the textual data;
   storing the check value and the textual data in a second block; and
   storing the second block in the blockchain where the first block is located.

3. The computer-implemented method of claim 1, wherein the non-textual data is image data.

4. The computer-implemented method of claim 1, further comprising:
   processing the first data record based on a processing rule corresponding to a textual data type;
   processing the second data record based on a processing rule corresponding to a non-textual data type; and
   sending a processed result to other blockchain nodes in the blockchain network.

5. The computer-implemented method of claim 1, further comprising:
   determining a data size of the second data record; and
   determining a storage location for the second data record based on the data size.

6. One or more non-transitory, computer-readable storage media storing instructions executable by a computer system implementing blockchain nodes of a blockchain network to perform operations comprising:
   receiving, at a blockchain node of the blockchain network, a first data record to be stored in a blockchain maintained by the blockchain network, wherein the first data record is medical data generated in association with a first medical practitioner of a first medical institution, wherein the blockchain network comprises a plurality of blockchain nodes that respectively belong to a plurality of different medical institutions;

preconfiguring a plurality of respective public-private key pairs for a plurality of medical practitioners employed by respective medical institutions of the plurality of the different medical institutions;

determining that the first data record comprises textual data;

in response to determining that the first data record comprises textual data, storing the textual data in the blockchain;

receiving, at the blockchain node of the blockchain network, a second data record to be stored in the blockchain, wherein the second data record is medical data generated in association with the first medical practitioner of the first medical institution;

determining that the second data record comprises non-textual data; and in response to determining that the second data record comprises non-textual data:
  generating a digest representing the non-textual data, wherein the digest is smaller in size than the non-textual data;
  establishing a mapping relationship between the digest and a data identifier of the non-textual data;
  storing the non-textual data at a database in accordance with the mapping relationship, wherein records of the database are not stored on the blockchain;
  generating an encrypted version of the digest using a user-specific key of a public-private key pair corresponding to a user identifier of the non-textual data;
  storing the encrypted version of the digest in the blockchain;

generating, for a second medical practitioner of a different second medical institution, a digital signature for the second medical practitioner to access non-textual patient data generated by a plurality of different medical institutions maintaining blockchain nodes of the blockchain network, including encrypting information associated with the second medical practitioner using a private key of the second medical practitioner;

receiving, from the second medical practitioner of the different second medical institution, a data query request for the second medical practitioner of the different second medical institution to access the non-textual data generated by the first medical institution, wherein the data query request includes the digital signature of the second medical practitioner and a queried user identifier;

authenticating the second medical practitioner based on the digital signature of the second medical practitioner;

determining a data access permission of the second medical practitioner, wherein the data access permission is determined based on a medical staff level of the second medical practitioner;

determining, based on the data access permission, that the second medical practitioner is authorized to access the non-textual data associated with the data query request;

in response, determining the digest of the non-textual data associated with the data query request;

sending the digest of the non-textual data to the database;

receiving the non-textual data that corresponds to the digest of the non-textual data and that is returned by the database;

verifying the non-textual data received from the database based on the digest of the non-textual data;

in response to a successful verification, selecting a query result satisfying the data access permission from the non-textual data corresponding to the queried user identifier; and sending the query result satisfying the data access permission to the second medical practitioner.

7. The non-transitory, computer-readable medium of claim 6, wherein storing the textual data in the blockchain comprises:
  determining a check value of a first block comprising the user identifier of the textual data;
  storing the check value and the textual data in a second block; and
  storing the second block in the blockchain where the first block is located.

8. The non-transitory, computer-readable medium of claim 6, wherein the non-textual data is image data.

9. The non-transitory, computer-readable medium of claim 6, the operations further comprising:
  processing the first data record based on a processing rule corresponding to a textual data type;
  processing the second data record based on a processing rule corresponding to a non-textual data type; and
  sending a processed result to other blockchain nodes in the blockchain network.

10. The non-transitory, computer-readable medium of claim 6, the operations further comprising:
  determining a data size of the second data record; and
  determining a storage location for the second data record based on the data size.

11. A computer-implemented system implementing blockchain nodes of a blockchain network, the system comprising:
  a plurality of computers; and
  one or more computer memory devices interoperably coupled with the plurality of computers and having tangible, non-transitory, machine-readable media storing one or more instructions that, when executed by the plurality of computers, perform operations comprising:
    receiving, at a blockchain node of the blockchain network, a first data record to be stored in a blockchain maintained by the blockchain network, wherein the first data record is medical data generated in association with a first medical practitioner of a first medical institution, wherein the blockchain network comprises a plurality of blockchain nodes that respectively belong to a plurality of different medical institutions;
    preconfiguring a plurality of respective public-private key pairs for a plurality of medical practitioners employed by respective medical institutions of the plurality of the different medical institutions;
    determining that the first data record comprises textual data;
    in response to determining that the first data record comprises textual data, storing the textual data in the blockchain;
    receiving, at the blockchain node of the blockchain network, a second data record to be stored in the blockchain, wherein the second data record is medical data generated in association with the first medical practitioner of the first medical institution;
    determining that the second data record comprises non-textual data; and in response to determining that the second data record comprises non-textual data:
    generating a digest representing the non-textual data, wherein the digest is smaller in size than the non-textual data;
    establishing a mapping relationship between the digest and a data identifier of the non-textual data;
    storing the non-textual data at a database in accordance with the mapping relationship, wherein records of the database are not stored on the blockchain;
    generating an encrypted version of the digest using a user-specific key of a public-private key pair corresponding to a user identifier of the non-textual data;
    storing the encrypted version of the digest in the blockchain;
generating, for a second medical practitioner of a different second medical institution, a digital signature for the second medical practitioner to access non-textual patient data generated by a plurality of different medical institutions maintaining blockchain nodes of the blockchain network, including encrypting information associated with the second medical practitioner using a private key of the second medical practitioner;
receiving, from the second medical practitioner of the different second medical institution, a data query request for the second medical practitioner of the different second medical institution to access the non-textual data generated by the first medical institution, wherein the data query request includes the digital signature of the second medical practitioner and a queried user identifier;
authenticating the second medical practitioner based on the digital signature of the second medical practitioner;
determining a data access permission of the second medical practitioner, wherein the data access permission is determined based on a medical staff level of the second medical practitioner;
determining, based on the data access permission, that the second medical practitioner is authorized to access the non-textual data associated with the data query request;
in response, determining the digest of the non-textual data associated with the data query request;
sending the digest of the non-textual data to the database;
receiving the non-textual data that corresponds to the digest of the non-textual data and that is returned by the database;
verifying the non-textual data received from the database based on the digest of the non-textual data;
in response to a successful verification, selecting a query result satisfying the data access permission from the non-textual data corresponding to the queried user identifier; and
sending the query result satisfying the data access permission to the second medical practitioner.

12. The computer-implemented system of claim 11, wherein storing the textual data in the blockchain comprises:
    determining a check value of a first block comprising the user identifier of the textual data;
    storing the check value and the textual data in a second block; and
    storing the second block in the blockchain where the first block is located.

13. The computer-implemented system of claim 11, wherein the non-textual data is image data.

14. The computer-implemented system of claim 11, the operations further comprising:
    processing the first data record based on a processing rule corresponding to a textual data type;
    processing the second data record based on a processing rule corresponding to a non-textual data type; and
    sending a processed result to other blockchain nodes in the blockchain network.

15. The computer-implemented system of claim 11, the operations further comprising:
    determining a data size of the second data record; and
    determining a storage location for the second data record based on the data size.

* * * * *

UNITED STATES PATENT AND TRADEMARK OFFICE
CERTIFICATE OF CORRECTION

PATENT NO. : 11,315,666 B2
APPLICATION NO. : 16/422618
DATED : April 26, 2022
INVENTOR(S) : Shifeng Wang It is certified that error appears in the above-identified patent and that said Letters Patent is hereby corrected as shown below:

On the Title Page

Column 1 (item (72)), Line 1, delete "Hanzhou" and insert -- Hangzhou --.

In the Claims

Column 20, Line 61, in Claim 6, delete "media" and insert -- medium --.

Signed and Sealed this
Nineteenth Day of July, 2022

*Katherine Kelly Vidal*

Katherine Kelly Vidal
*Director of the United States Patent and Trademark Office*